(12) United States Patent
Jackson et al.

(10) Patent No.: US 11,137,830 B1
(45) Date of Patent: Oct. 5, 2021

(54) INTERACTIVE COMPUTING SYSTEM AND CONTROL DEVICE

(71) Applicants: Benjamin G. Jackson, Belmont, CA (US); Seung Wook Kim, Cupertino, CA (US); David H. Bloom, San Francisco, CA (US); Brenton A. Baugh, Los Altos Hills, CA (US); Steven J. Taylor, San Jose, CA (US); Madeleine S. Cordier, San Francisco, CA (US)

(72) Inventors: Benjamin G. Jackson, Belmont, CA (US); Seung Wook Kim, Cupertino, CA (US); David H. Bloom, San Francisco, CA (US); Brenton A. Baugh, Los Altos Hills, CA (US); Steven J. Taylor, San Jose, CA (US); Madeleine S. Cordier, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 318 days.

(21) Appl. No.: 16/130,476

(22) Filed: Sep. 13, 2018

Related U.S. Application Data (60) Provisional application No. 62/561,718, filed on Sep. 22, 2017.

(51) Int. Cl.
*G06F 3/01* (2006.01)
*G06F 3/0346* (2013.01)
(Continued)

(52) U.S. Cl.
CPC .......... *G06F 3/016* (2013.01); *G06F 3/0346* (2013.01); *G06T 19/006* (2013.01); *A61B 34/25* (2016.02); *A61B 34/76* (2016.02)

(58) Field of Classification Search
CPC ..... G06F 3/016; G06F 3/0346; G06T 19/006; A61B 34/25; A61B 34/76
See application file for complete search history.

(56) References Cited

U.S. PATENT DOCUMENTS 5,483,261 A * 1/1996 Yasutake ............... G06F 3/0425
178/18.03
6,297,838 B1 * 10/2001 Chang ....................... G06F 1/16
345/156

(Continued)

FOREIGN PATENT DOCUMENTS

CN       101261781 A     9/2008

OTHER PUBLICATIONS

Hatzfeld, C., et. al., "Engineering Haptic Devices: A Beginner's Guide", Springer, Sep. 15, 2014, p. 77 (1 p).

(Continued)

*Primary Examiner* — Dmitriy Bolotin
(74) *Attorney, Agent, or Firm* — Young Basile Hanlon & MacFarlane, P.C.

(57) ABSTRACT

A control device for an interactive computing system includes a first elongated member, a second elongated member, and a biasing actuator. The first elongated member and the second elongated member are pivotably coupled at a pivot axis. The biasing actuator is coupled to the first elongated member and the second elongated member to provide an output torque between the first elongated member and the second elongated member about the pivot axis. The control device is configured to receive user input for controlling a virtual device displayed by the interactive computing system to visually resemble a physical device. The biasing actuator is controllable to provide tactile feedback to simulate physical behavior of the physical device. The control device is movable freely in space.

41 Claims, 8 Drawing Sheets

(51) Int. Cl.
*G06T 19/00* (2011.01)
*A61B 34/00* (2016.01)

(56) References Cited

U.S. PATENT DOCUMENTS

| | | | |
|---|---|---|---|
| 6,377,011 B1 | 4/2002 | Ben-Ur | |
| 6,593,907 B1 | 7/2003 | Demers et al. | |
| 6,597,347 B1* | 7/2003 | Yasutake | G06F 3/0338 345/173 |
| 7,155,316 B2 | 12/2006 | Sutherland et al. | |
| 8,845,667 B2* | 9/2014 | Cruz Hernandez | A61B 34/76 606/174 |
| 10,001,885 B2* | 6/2018 | Pance | G06F 1/1616 |
| 10,168,873 B1* | 1/2019 | Holz | G06F 3/011 |
| 2002/0120188 A1* | 8/2002 | Brock | A61B 5/0086 600/407 |
| 2010/0291520 A1* | 11/2010 | Kurenov | A61B 17/0491 434/262 |
| 2012/0176319 A1* | 7/2012 | Miyako | G06F 3/04812 345/167 |
| 2013/0023917 A1* | 1/2013 | Cruz Hernandez | A61B 17/28 606/174 |
| 2014/0088941 A1* | 3/2014 | Banerjee | A61B 34/30 703/11 |
| 2017/0108930 A1* | 4/2017 | Banerjee | A61B 90/37 |

OTHER PUBLICATIONS

3DSYSTEMS, "Haptic Devices and Toolkits", <https://web.archive.org/web/20170918181629/http://sivirt.utsa.edu/Documents/Manuals/Haptics%20Omni.pdf>, dated Sep. 18, 2017, downloaded Sep. 13, 2018, (4 pp).

Okamura, A. M., et. al., "The Haptic Scissors: Cutting in Virtual Environments", <http://citeseerx.ist.psu.edu/viewdoc/download?doi=10.1.1.88.1945&rep=rep1&type=pdf>, 2003, downloaded Sep. 11, 2018, (6 pp).

Powers, M., et. al., "Surgical Scissors Extension Adds the 7th Axis of Force Feedback to the Freedom 6S", NRC Publications Archive (NPArC), https://nparc.nrc-cnrc.gc.ca/nparc/eng/view/object/?id=db08ba4a-b595-4039-b99a-1dcceba658fb, Proceedings of the 15th Annual Medicine Meets Virtual Reality Conference, Feb. 9, 2007 (7 pp).

* cited by examiner

INTERACTIVE COMPUTING SYSTEM AND CONTROL DEVICE

CROSS-REFERENCE TO RELATED APPLICATION(S)

This application claims priority to and the benefit of U.S. Provisional Patent Application No. 62/561,718, filed Sep. 22, 2017, the entire disclosure of which is incorporated by reference herein.

TECHNICAL FIELD

This disclosure relates to an interactive computing system and a control device therefor and, in particular, a control device that provides physical feedback to the user.

BACKGROUND

Interactive computing systems, such as gaming consoles and simulators, receive user inputs with a physical control for controlling virtual objects. The virtual objects may, for example, include various types of virtual devices that resemble familiar physical devices and that are controllable by the user with the control device. For example, the user may use the physical control device to control characters in video games or flight controls in flight simulators. Conventional control devices, however, often receive user inputs via physical interactions that are unfamiliar to the user as compared to the virtual device controlled thereby, and often provide no physical feedback or only unfamiliar physical feedback relative to the virtual device. For example, conventional control devices may be configured as a gaming controller having depressible buttons for controlling movement and actions of a virtual device. The physical action of depressing a button, however, may not familiar to the user by not resembling physical behavior of the physical device resembled by the virtual device.

SUMMARY

Disclosed herein are implementations of interactive computing systems and control devices therefor. In one implementation, a control device for an interactive computing system includes a first elongated member, a second elongated member, and a biasing actuator. The first elongated member and the second elongated member are pivotably coupled at a pivot axis. The biasing actuator is coupled to the first elongated member and the second elongated member to provide an output torque between the first elongated member and the second elongated member about the pivot axis. The control device is configured to receive user input for controlling a virtual device displayed by the interactive computing system to visually resemble a physical device. The biasing actuator is controllable to provide tactile feedback to simulate physical behavior of the physical device. The control device is movable freely in space.

The control device may further include one or more additional actuators that include one or more of a brake actuator that resists input torque between the first elongated member and the second elongated member about the pivot axis, an inertial actuator coupled to one of the first elongated member or the second elongated member, and a mass actuator that moves a center of gravity of the control device. The one or more additional actuators are controllable to provide the tactile feedback.

The control device may include one or more sensors for receiving user input, which may include one or more of a position sensor for determining a relative angular position between the first elongated member and the second elongated member about the pivot axis, a torque sensor for determining a input torque applied to the first elongated member and the second elongated member about the pivot axis, and an orientation sensor determining an orientation of the control device.

In another implementation, an interactive computing system may include the control device, a display device, and a computing device in communication with the control device and the display device. The display device displays the virtual device to visually resemble the physical device, and the biasing actuator is controlled to provide the tactile feedback resembling physical behavior of the physical device.

In another implementation, method for operating the interactive computing system includes, receiving user inputs with the control device, changing an appearance of the virtual device according to the user inputs with the display device, and providing tactile feedback with the control device by controlling the output torque the control device with the biasing actuator.

The providing of the tactile feedback may also include controlling outputs of one or more of a brake actuator to resist movement between the first elongated member and the second elongated member, an inertial actuator to vibrate one or more of the first elongated member or the second elongated member, or a mass actuator to move a center of gravity of the control device.

In another implementation, an interactive computing system includes a user control device, a display device, and a computing device. The user control device is movable independent of a real environment. The user control device includes first and second members that are pivotably coupled to each other, a sensor for receiving a user input from a user apply input torque between the first and second members, and a biasing actuator that provides output torque between the first and second members. The display device displays a virtual device. The computing device is in communication with the user control device and the display device. The computing device receives the user input from the user control device, controls the display device to change an appearance of the virtual device according to the user input, and controls the biasing actuator to provide the output torque as tactile feedback corresponding to the change in appearance of the virtual device.

In another implementation, a method of operating an interactive computing system includes: receiving user input from a control device having two members that are pivotable relative to each other and a biasing actuator that applies output torque between the two members, wherein the control device is freely movable; changing with a display device an appearance of a virtual device according to the user input; and providing tactile feedback with the control device by controlling the output torque of the control device with the biasing actuator.

DETAILED DESCRIPTION

Disclosed herein are embodiments of interactive computing systems and control devices that receive physical inputs and provide physical outputs (e.g., feedback or tactile feedback) for manipulating a virtual device. The physical outputs provided by the control device simulate or resemble physical behavior of a physical device simulated or resembled by the virtual device. As a result, the user may more intuitively control the virtual devices with the input device and may have a more immersive experience with the interactive computing system.

More particularly, the control device physically mimics or resembles the physical interactions with tools or devices that are operated by biasing one portion of the tool toward and/or away from another portion of the tool. Such physical tools may, for example, be a type of handheld tool that is operated when grasped, compressed, and/or expanded by the user's hand(s), such as different types of grabbing devices (e.g., pliers, tongs, etc.), cutting devices (e.g., scissors, garden shears, etc.), and other devices or tools (e.g., staplers, nut crackers, etc.). The control device receives user inputs by the user pressing together or pulling apart portions of the control device that are opposed to each other (e.g., by applying forces thereto and/or causing movement thereof). The control device provides the user with physical outputs (e.g., tactile feedback) by causing movement between the portions, resisting movement between the portions, vibrating the portions, changing a center of gravity of the control device, or combinations thereof. Such physical outputs may simulate physical characteristics (e.g., physical behavior) of the physical tool, such as compressibility, return force, friction, vibration characteristics, material properties, and center of gravity, among other characteristics. Such outputs may also simulate physical characteristics of a physical object and behavior of the physical tool interacting with the physical object, such as compressibility of the object and friction between the physical device and the physical object. For illustration purposes, the tactile feedback provided by the physical output of the control device may vary according to whether the resembled physical device is a pair of plastic scissors, metal scissors, or sprung garden shears. Further, the plastic scissors, metal scissors, and sprung garden shears may each interact differently with different types of virtual subjects, such as when cutting paper, fabric, or a stick (e.g., having different movement/resistance representing the stiffness of the object, different vibration representing texture or friction as the object is cut, and different and/or moving centers of gravity as the object is lifted).

Figure 1:
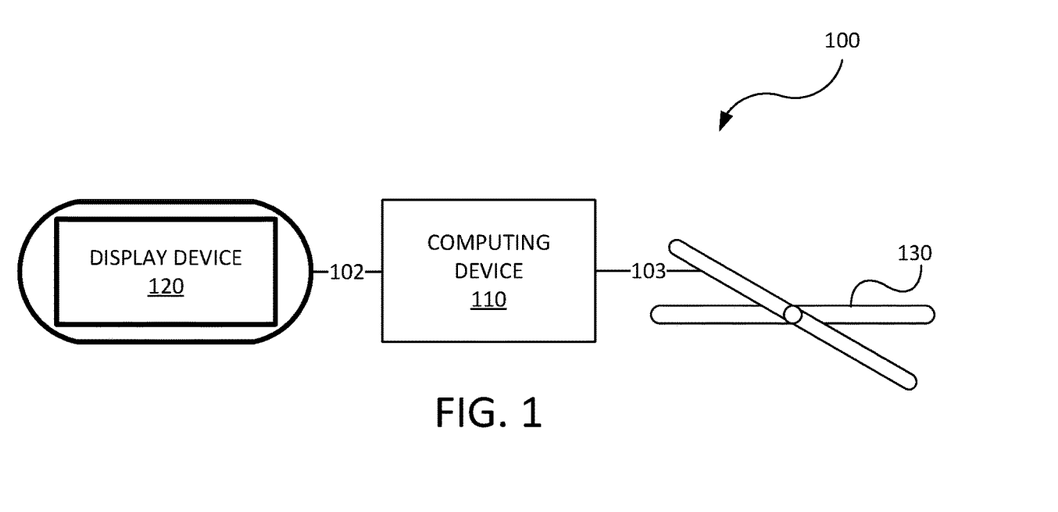
FIG. 1 is a schematic view of an interactive computing system.

Referring to FIG. 1, an interactive computing system 100 generally includes a computing device 110, a display device 120, and a control device 130. The computing device 110 receives inputs from and provides outputs to the display device 120 and the control device 130. The display device 120 displays a virtual scene (discussed further below), which may include a virtual device that may interact with a virtual subject and/or move within a virtual environment. The control device 130 receives physical inputs from a user and provides physical outputs to the user as the user physically manipulates the control device 130, so as to virtually manipulate the virtual device to interact with the virtual subjects and/or the virtual environment displayed by the display device 120. The control device 130 may also be referred to as a tactile control device, a handheld control device, a user control device, or a physical control device. As referenced above and as described in further detail below, the control device 130 may physically replicate one or more types of conventional physical devices (e.g., tools or instruments) that are operated by moving two portions toward and/or away from each other (e.g., via pivoting).

The computing device 110 is in electronic communication with the display device 120 with a communications channel 102 and with the control device 130 with another communications channel 103. The communications channel 102 and/or the communications channel 103 may provide wired or wireless communication. As a result, the interactive computing system 100, as controlled by the computing device 110, may produce visual outputs with the display device 120 to be viewed by the user and may also receive tactile inputs from and control tactile outputs to the user via the control device 130. The interactive computing system 100 may be configured as a virtual reality system that generates and displays a virtual environment and virtual objects simultaneously, an augmented reality system that generates and displays virtual objects that overlay a real environment, and/or a mixed reality system that generates and displays virtual objects with respect (e.g., in spatial relation) to a real environment. In the case of augmented reality and mixed reality, the real environment may be viewed directly by the user, such as through a lens off of which the virtual environment and the virtual objects are reflected, or may be displayed, such as from being observed by a video camera of the interactive computing system 100.

Figure 2:
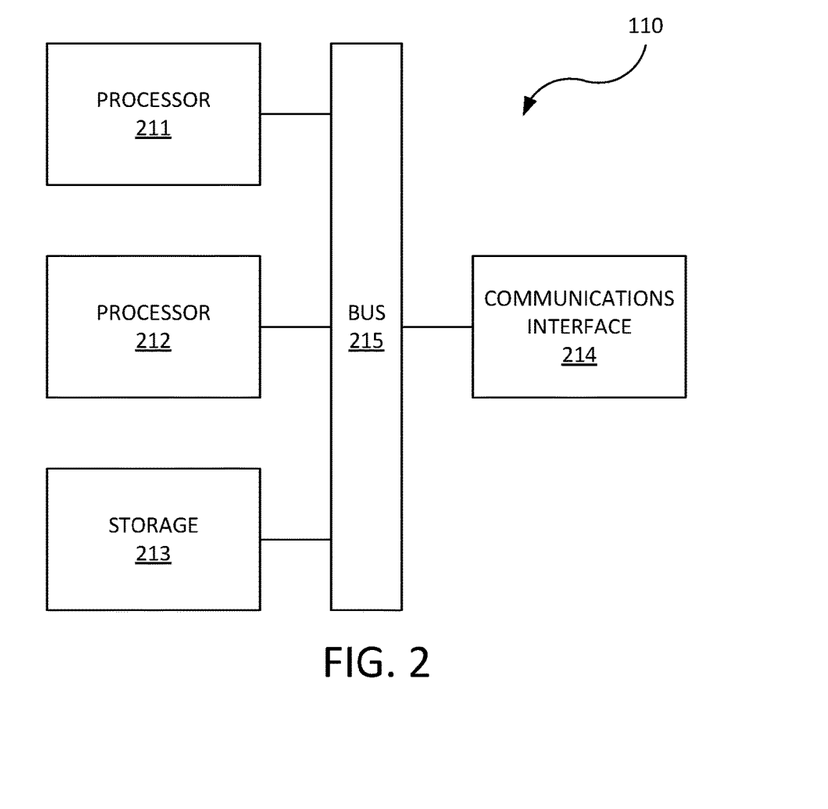
FIG. 2 is a schematic view of a computing device of the interactive computing system of FIG. 1.

Referring to FIGS. 1 and 2, the computing device 110 is generally configured to process, send, and receive signals to and from the display device 120 and the control device 130 to control the visual and tactile outputs to the user and to receive inputs from the user. The computing device 110 may have an example hardware configuration as shown in FIG. 2 and generally include a processor 211, a memory 212, a storage device 213, a communications interface 214, and a bus 215 interconnecting the other components for communication therebetween. The processor 211 is operable to execute computer program instructions and perform operations described by the computer program instructions. As an example, the processor may be a central processing unit, or other conventional processing device. The memory 212 may, be a short-term information storage device, such as a random-access memory module or other volatile, high-speed, short-term storage device. The storage device 213 may be a long-term information storage device, such as a hard drive, such as a hard disk drive, a solid-state drive, or other non-volatile information storage device. The communications interface 214 is configured to receive inputs (e.g., signals) and provide outputs (e.g., signals) to and from communications interfaces, for example, of the display device 120 and the control device 130. The communications interface 214 may, for example, be configured to send and receive wired or wireless signals via suitable communications protocols, for example, via the communications channel 102 and the communications channel 103. The computing device 110 may be configured in other manners, for example, by being a distributed computing device (e.g., having operations performed cooperatively by multiple computing devices, or having components thereof distributed among different devices).

Figure 3:
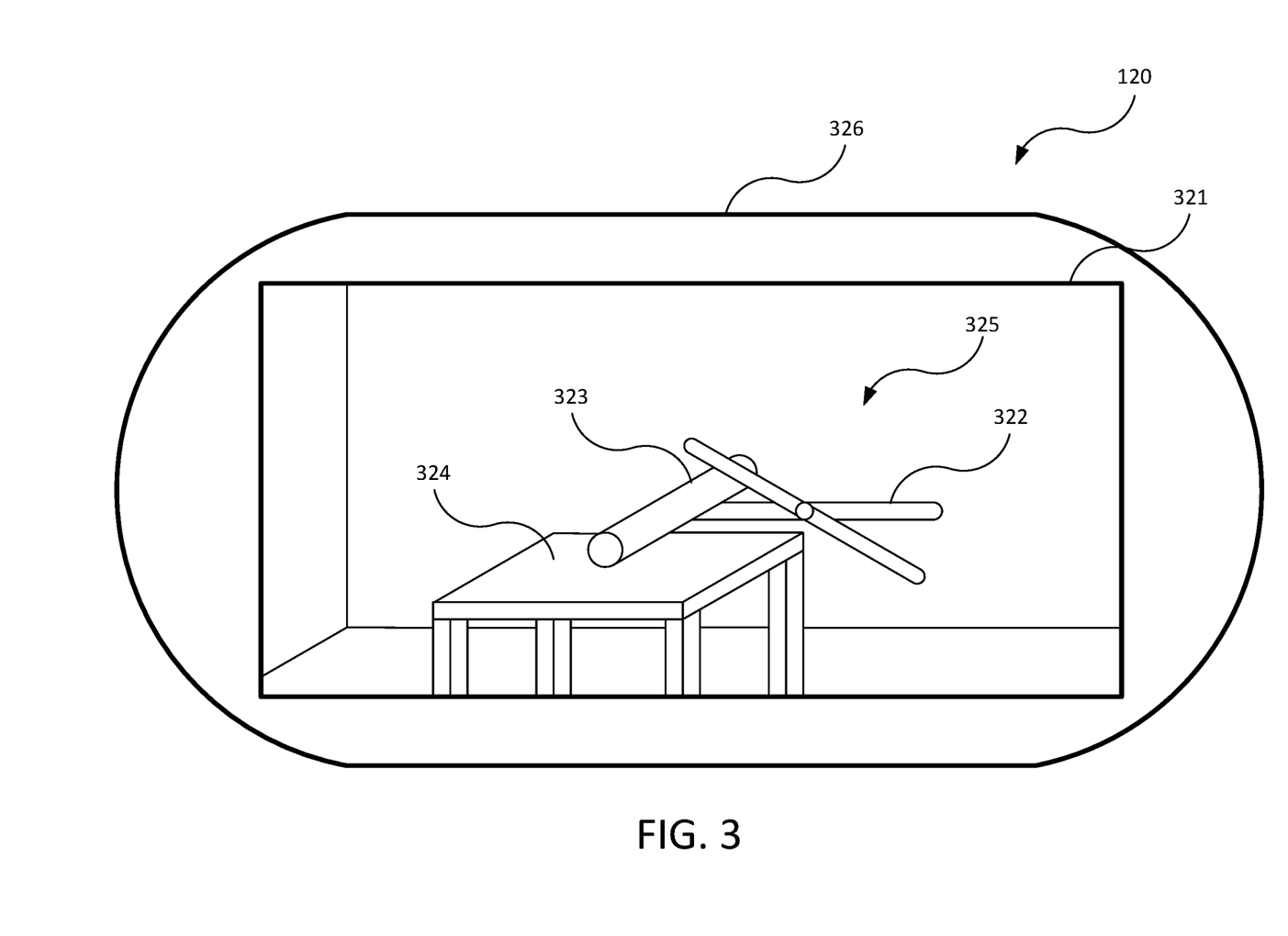
FIG. 3 is a view of a display device of the interactive computing system displaying a virtual scene.

Referring to FIGS. 1 and 3, the display device 120 includes a display 321 that displays a virtual scene containing one or more virtual objects, such as virtual objects 322-324 and a virtual environment 325 containing the virtual objects 322-324. The virtual objects may, for example, include a virtual device 322 and may also include a virtual subject 323 and/or a virtual environment object 324. The virtual device 322 is a graphic having an appearance that visually resembles a physical device (e.g., the graphic illustrates or depicts the physical device). The virtual device 322 changes in appearance (e.g., moving or changing in shape or state) corresponding to the inputs received from and the tactile outputs provided to the user with the control device 130. Such changes in the appearance of the virtual device 322 resemble movement of the physical device resembled by the virtual device 322, so as to simulate operating the physical device and/or moving the physical device in space. The display device 120 may also include speakers so as to provide audible outputs corresponding to manipulation of the virtual device and the virtual object, for example, representing a noise from the physical device engaging the physical object (e.g., when cutting cardboard).

The virtual subject 323 is a graphic having an appearance that resembles a physical object. The virtual subject 323 changes in appearance in manners corresponding to movement of the virtual device 322 to manipulate the virtual subject 323, for example, to simulate changing a form of the physical object (e.g., compressing and/or dividing into multiple portions) and/or moving the physical object in space.

The virtual environment object 324 includes a graphic having an appearance that resembles another object, which may be engaged by the virtual device 322 and/or the virtual subject 323. The virtual environment 325 includes graphics that provide a visual representation of an environment containing the virtual device 322, the virtual subject 323, and the virtual environment object 324. As the user physically manipulates the control device 130, the appearances of the virtual device 322 and/or the virtual subject 323 may change, for example, by moving relative to the virtual environment 325 and/or by changing shape.

For illustration purposes, as shown in FIG. 3, the virtual device 322 is a pair garden shears, the virtual subject 323 may be a wood stick, the virtual environment object 324 is a table, and the virtual environment 325 is a room having walls and a floor. Though not shown, the virtual scene may also display a virtual operator, such as a representation of a person's hand grasping the virtual device 322.

The interactive computing system 100 may be reconfigurable such that the virtual objects 322-324 and the virtual environment 325 may be changed, so as to provide the user with different experiences. As a result, the tactile feedback provided by the control device 130 may be changed according to the different physical characteristics (e.g., physical behavior) of the physical device and/or the physical object resembled by the virtual device and the virtual subject, respectively. For example, the virtual device 322 may be scissors and the virtual subject 323 may be paper, whereby the tactile feedback provided by the control device 120 and changes to the virtual scene resemble the scissors cutting the paper. At a subsequent time, the virtual device 322 may instead be tongs and the virtual subject 323 is lettuce, whereby the tactile feedback provided by the control device 120 and changes to the virtual scene resemble the tongs squeezing the lettuce.

The display device 120 may, as shown, be a headset to be worn by the user (e.g., a head-mounted display unit or HMD). The display device 120 may include a flange 326 that blocks from view of the user the physical environment in which the user is positioned. Alternatively, the display device 120 may be another portable device, such as laptop computer, a tablet computer, or a smartphone, or may be a substantially stationary device, such as one or more displays associated with a desktop computer or gaming console.

The computing device 110 may, as referenced previously, be in wired or wireless communication with the display device 120. Alternatively, the display device 120 may include the computing device 110 internally thereto. The display device 120 may also include a controller (not shown), which may be configured similar to the computing device 110 described with respect to FIG. 2.

Figure 4:
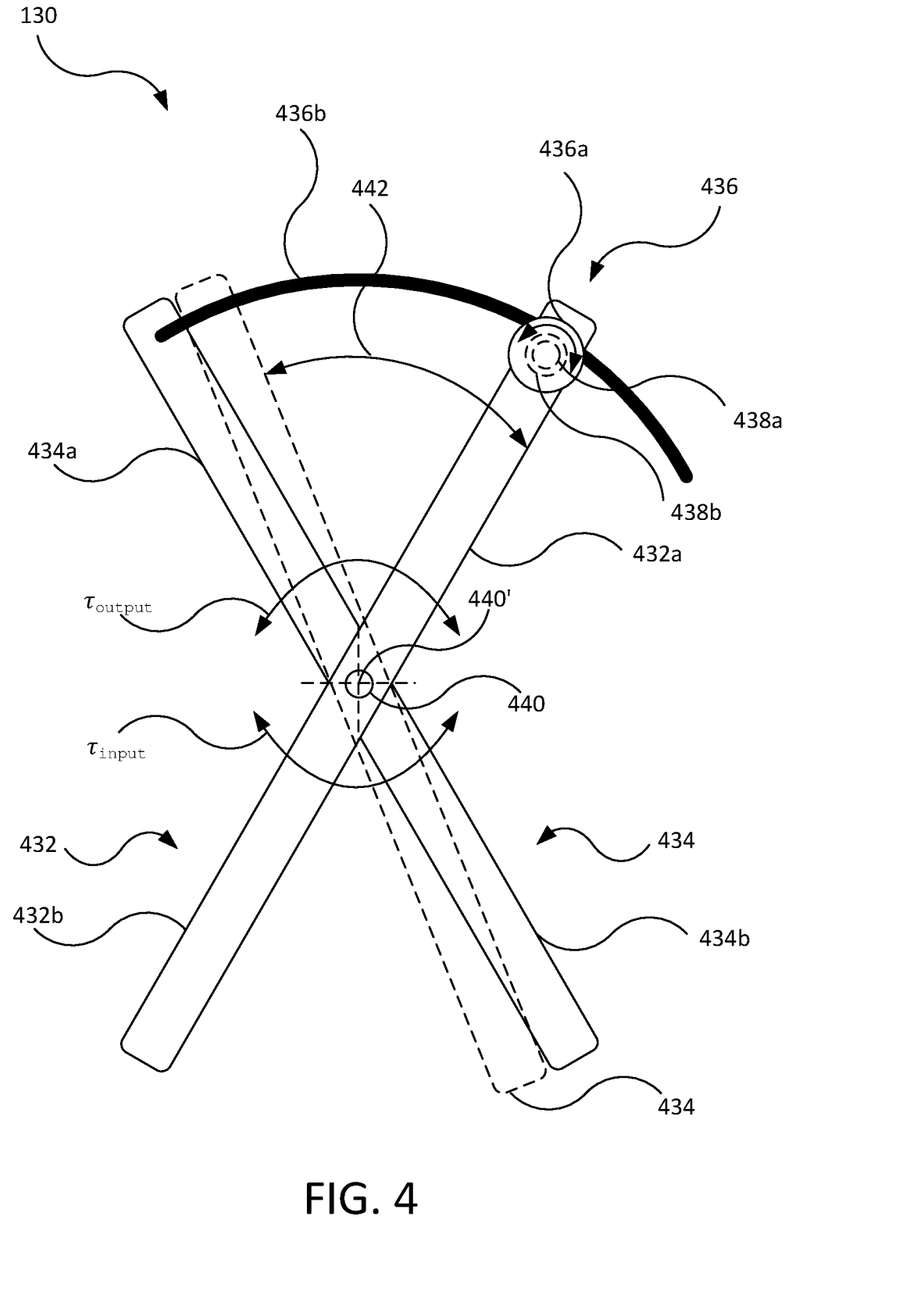
FIG. 4 is a view of a control device of the interactive computing system of FIG. 1.

Referring to FIGS. 1, 3, and 4, the control device 130 is a handheld device configured to receive input from the user and provide tactile output to the user. The control device 130 is configured to simulate physical behavior of a type of physical device visually resembled by the virtual device 322. Thus, as the user provides the tactile inputs to manipulate the virtual device 322 and/or to interact with the virtual subject 323 and/or the virtual environment object 324, the control device 130 provides physical outputs that simulate or resemble the physical behavior of the device resembled visually by the virtual device 322.

The control device 130 may be configured to move freely in space, while still receiving inputs from the user. That is, the control device 130 may be movable independent of the real environment. For example, the control device 130 is not physically coupled to a ground location with a mechanical device for receiving user inputs related to moving the control device in space (e.g., the control device 130 may not include or be physically coupled to a base relative to which movement of the control device 130 is measured with a mechanical device). Without such a mechanism, the control device 130 may still receive user inputs related to operation of the control device 130 (e.g., angular position, angular acceleration, and/or torque between elongated members 432, 434 discussed below) and/or movement of the control device 130 in real space (e.g., with the orientation sensors 950 and/or the external observation cameras discussed below). The control device 130 may, when in wired communication with the computing device 110, still be considered freely movable in space.

The control device 130 is in wired or wireless communication with the communications interface 214 of the computing device 110. The control device 130 may additionally include a controller (not shown) that, for example, processes various input and output signals to and from and the actuators and/or the sensors thereof, and/or the computing device 110. The controller of the control device 130 may, for example, be configured similar to the computing device 110 described with respect to FIG. 2.

The control device 130 generally includes a first elongated member 432, a second elongated member 434, a biasing actuator 436, and one or more sensors, such as a position sensor 438a and a torque sensor 438b. The biasing actuator 436 is configured with the first elongated member 432 and the second elongated member 434 to provide physical outputs that provide tactile feedback to the user, while the one or more sensors are configured to receive physical inputs from the user and/or control the one or more actuators. As discussed in further detail below, variations of the control device 130 may include different and/or additional actuators, such as brake actuators, inertial actuators, and mass actuators. The one or more sensors may, for example, include torque sensors, touch sensors, and/or inertial sensors.

The first elongated member 432 and the second elongated member 434 are pivotably coupled to each other at a pivot axis 440', for example, by a shaft 440 (e.g., pin). The first elongated member 432 and the second elongated member 434 pivot relative to each other over a range of motion 442, for example, between a closed configuration (e.g., fully or partially closed or collapsed position or configuration), which is generally illustrated by the first elongated member 432 being in dashed lines, and an open configuration (e.g., fully or partially open or expanded position or configuration). The range of motion of the control device 130 may, for example, be up to 110 degrees, smaller, or larger. The elongated members 432, 434, while depicted for illustrative purposes as being straight and of the same size (e.g., length and width), may have different shapes and/or sizes from each other and/or as shown (e.g., instead being bent or curved, longer or shorter, wider or narrower). Furthermore, the elongated members 432, 434, while depicted for illustrative purposes as unitary structures, may be assemblies formed of multiple components. The elongated members 432, 434 may also be referred to as two members.

The pivot axis 440' may be fixed relative to the first elongated member 432 and the second elongated member 434 (as shown in FIG. 4). In other embodiments, the pivot axis 440' may move along one or both of the first elongated member 432 and the second elongated member 434 (e.g., using lead screws), as is illustrated by arrows shown in FIG. 9 in dash-dot lines. By moving the pivot axis 440' the control device 130 may provide tactile feedback corresponding to physical devices that have pivot axes at different locations relative to a user's hand (e.g., smaller and larger scissors having short and longer handles, fire tongs having longer handles, etc.).

The first elongated member 432 and the second elongated member 434 include distal portions 432a, 434a, respectively, and proximal portions 432b, 434b, respectively. The proximal portions 432b, 434b are configured to be grasped by a user, for example, by the user's hand. Thus, a user may press together or pull apart the proximal portions 432b, 434b to apply an input, which may be referred to as an input force or an input torque $\tau_{input}$ about the pivot axis 440' to the control device 130. The force applied by the user and/or the input torque $\tau_{input}$ may be referred to as a tactile input or user input.

Figure 9:
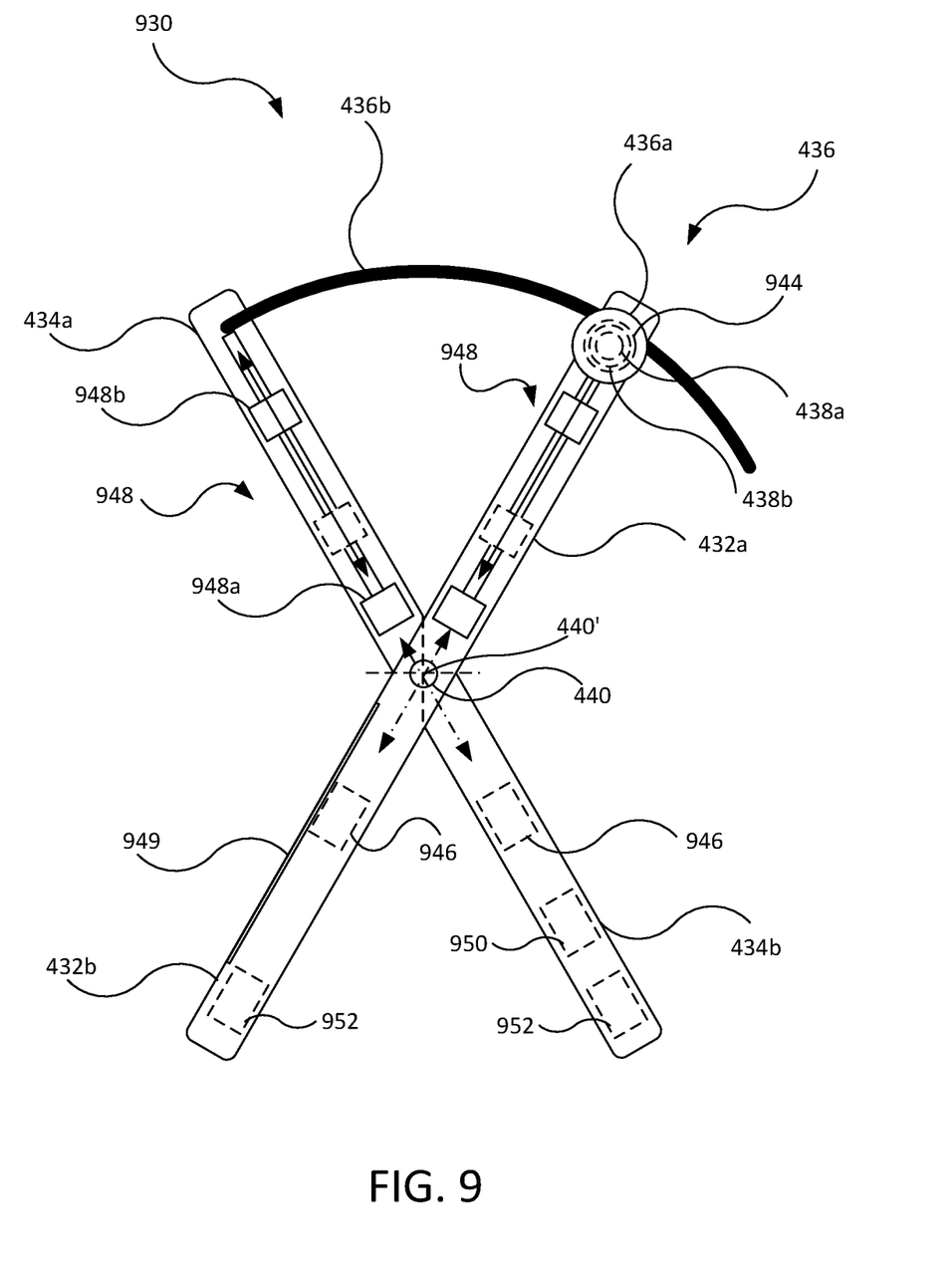
FIG. 9 is a view of another control device for use with the interactive computing system of FIG. 1.

Referring to FIG. 4, the biasing actuator 436 is configured to provide physical output to the user. The biasing actuator 436 is operable to bias or move the first elongated member 432 and the second elongated member 434 relative to each other by causing movement therebetween and resisting movement therebetween. For example, the biasing actuator 436 may be configured to provide an output from the control device 130, which may be expressed as output torque $\tau_{output}$ between the first elongated member 432 and the second elongated member 434, which resembles physical behavior of the physical device resembled by the virtual device. As discussed in further detail below, variations on the control device 130 may, however, include additional and different types of actuators that provide physical outputs in different manners from each other. For example, as shown in FIG. 9, a control device 930 may include the biasing actuator 436, brake actuators 944 (see FIG. 9; also referred to as a brake actuator or brake), inertial actuators 946 (see FIG. 9; also referred to as vibration actuators), and/or mass actuators 948 (see FIG. 9; also referred to as weight shifting actuators).

Still referring to FIG. 4, the biasing actuator 436 applied torque between and/or moves the first elongated member 432 relative to the second elongated member 434 to provide the tactile feedback to the user. The tactile feedback provided by the biasing actuator 436 may include active movement of the first elongated member 432 and the second elongated member 434 to move the proximal portions 432b, 434b toward and away from each other. Such active movement by the biasing actuator 436 may, for example, represent the tendency of physical devices resembled by the virtual device 322 to bias corresponding members toward and away from each other. Such physical devices may, for example, include springs that normally bias pivotable members toward or away from each other (e.g., sprung garden shears that are sprung open) or that have pivotable members that are moved by gravity (e.g., with pivotable members having more mass on one side of the pivot). Such active movement by the biasing actuator 436 may also, for example, represent interaction with physical objects resembled by the virtual subject 323 that press apart the resembled physical devices, such as a physical object being compressed by the pivotable members (e.g., a spring being compressed) or gravity acting on the physical object.

The tactile feedback from the biasing actuator 436 may also resist input from the user that might otherwise cause relative movement between the first elongated member 432 and the second elongated member 434. For example, the biasing actuator 436 provides the output torque $\tau_{output}$ to resist an input torque $\tau_{input}$ from the user applying force to the proximal portions 432b, 434b. Such movement resistance by the biasing actuator 436 may, for example, represent the tendency of the corresponding physical devices to resist movement between the corresponding members, such as friction between two blades of a pair of scissors. Such movement resistance by the biasing actuator 436 may also, for example, represent interaction with physical objects by the corresponding physical devices, such as resistance (e.g., the friction and compression) from the garden shears cutting through a branch, the scissors cutting through paper, and tongs grabbing and compressing an object.

The tactile feedback from the biasing actuator 436, whether active movement or movement resistance, may also vary with movement between the first elongated member 432 and the second elongated member 434. Such varied output may, for example, be a sudden increase or decrease in the output torque $\tau_{output}$ representing ends of the range of travel of the physical device or engagement or disengagement of the virtual device 322 with the virtual subject 323 (e.g., garden shears first engaging and then cutting through the branch). Such varied output may also, for example, be a pulsating of the output torque $\tau_{output}$ at a frequency representing characteristics of the physical device (e.g., detents or ratcheting features of the physical device) or texture of the virtual device 322 engaging the virtual subject 323 (e.g., scissors cutting a coarse fabric, nut cracker breaking a shell of a nut).

The biasing actuator 436 may, as shown, be connected to the distal portions 432a, 434a, respectively, of the first elongated member 432 and the second elongated member 434. The biasing actuator 436 forces the distal portions 432a, 434a toward and/or away from each to provide the output torque $\tau_{output}$ about the pivot axis 440'. As the biasing actuator 436 applies force between the distal portions 432a, 434a of the first elongated member 432 and the second elongated member 434, the proximal portions 432b, 434b (i.e., those grasped by the user) are forced toward or away from each other.

In one implementation, the biasing actuator 436 generally includes an electric motor 436a and a connecting member 436b. A first end of the connecting member 436b is connected to the distal portion 434a of the second elongated member 434, while the electric motor 436a is connected to the distal portion 432a of the first elongated member 432 and is operably connected to a second portion of the connecting member 436b. For example, the electric motor 436a and the connecting member 436b may be operably connected via toothed or frictional engagement, such that rotation of the electric motor 436a may pull toward or push away the distal portion 432a of the first elongated member 432 relative to the distal portion 434a of the second elongated member 434. As a result, the biasing actuator 436 may vary the output torque $\tau_{output}$ of the control device 130 to provide different tactile outputs to the user.

Figure 5:
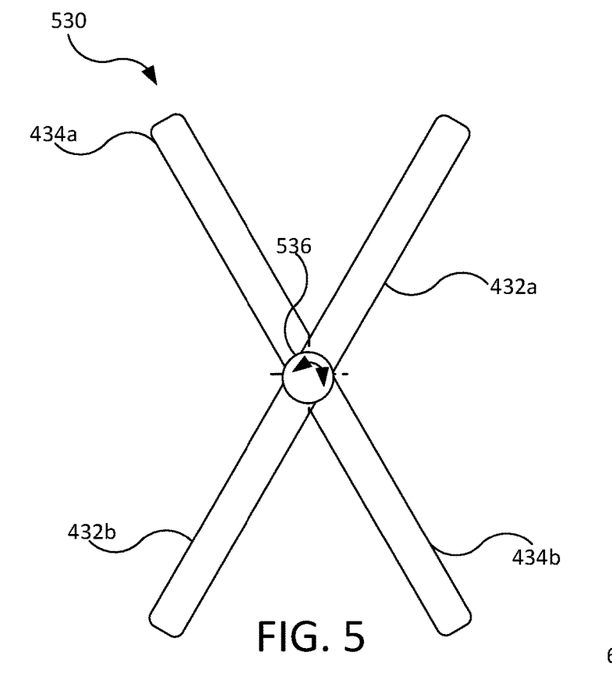
FIG. 5 is a view of another control device for use with the interactive computing system of FIG. 1.
Figure 6:
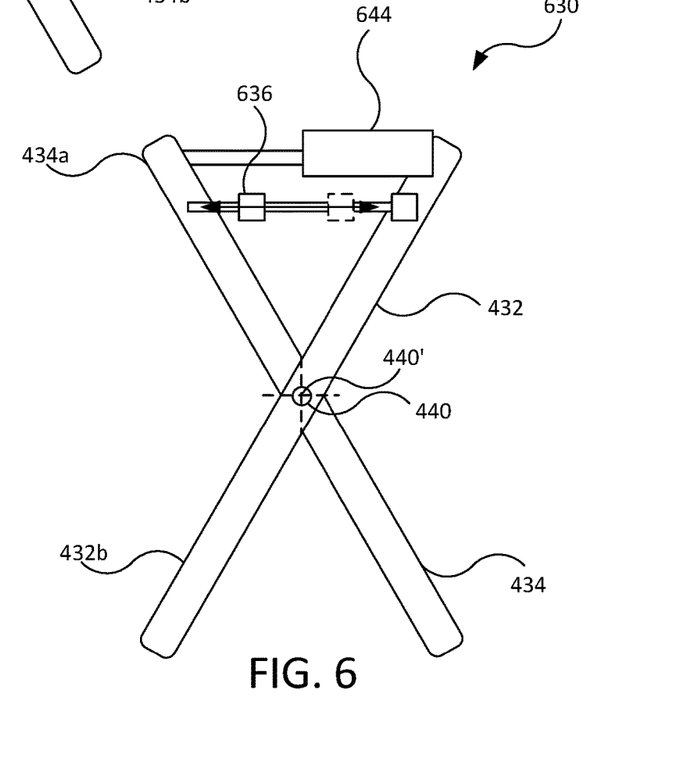
FIG. 6 is a view of another control device for use with the interactive computing system of FIG. 1.
Figure 7:
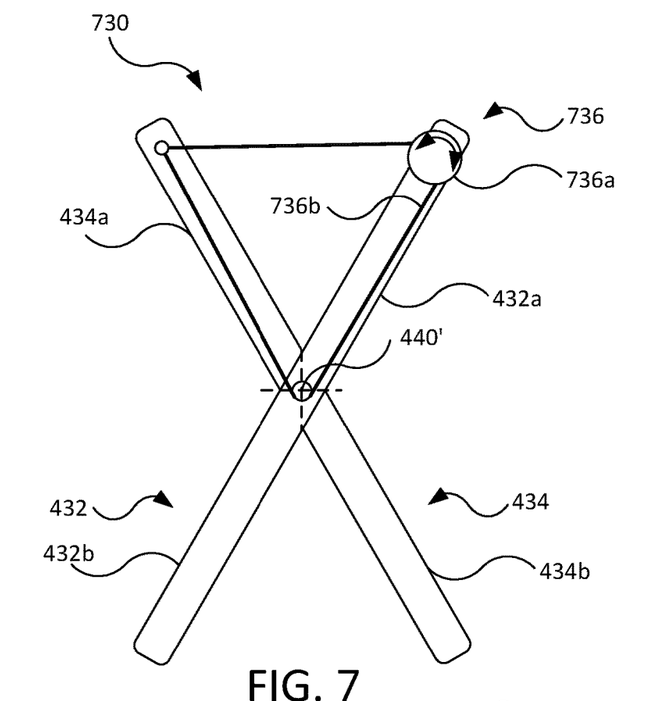
FIG. 7 is a view of another control device for use with the interactive computing system of FIG. 1.
Figure 8:
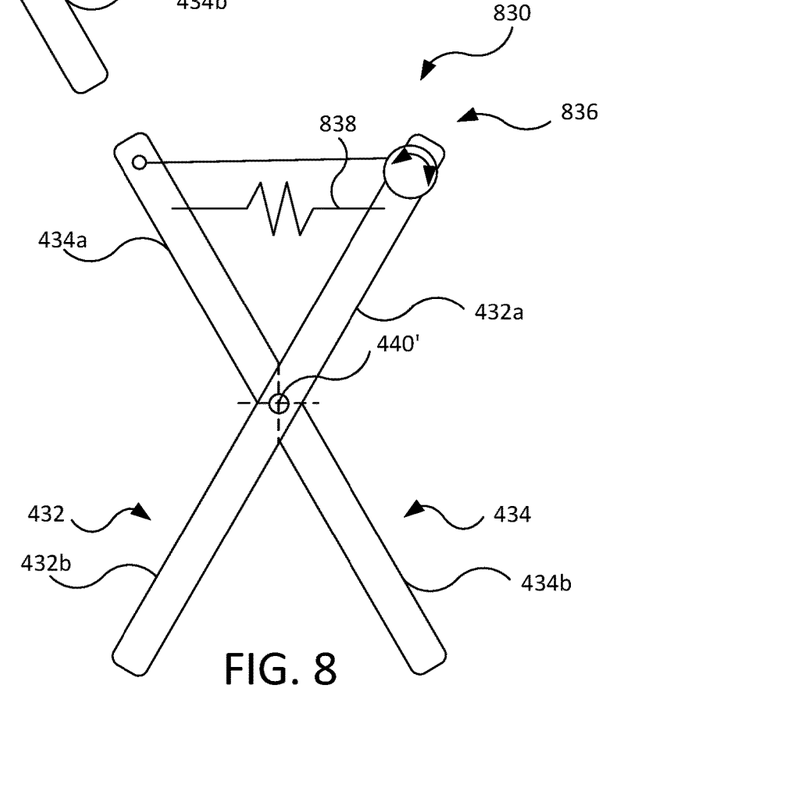
FIG. 8 is a view of another control device for use with the interactive computing system of FIG. 1.

The biasing actuator 436 may be configured in different manners to provide the output torque $\tau_{output}$. For example, as shown in FIG. 5, a control device 530 that is a variant of the control device 430 may instead include a biasing actuator 536 that is an electric motor located at the pivot axis 440'. For example, rotor and stator components of the electric motor of the biasing actuator 536 may, respectively, be coupled to the first elongated member 432 and the second elongated member 434. As another example shown in FIG. 6, another control device 630 includes biasing actuator 636 that is a linear actuator (e.g., a lead screw) extending between the distal portions 432a, 434a of the first elongated member 432 and the second elongated member 434. In a still further example shown in FIG. 7, another control device 730 includes a biasing actuator 736 that includes a capstan 736a operated by a motor to pull a cable 736b to pull the first elongated member 432 and the second elongated member 434 toward each other (e.g., the cable 736b extending directly therebetween) and/or apart from each other (e.g., the cable 736b instead or additionally extending therebetween around the pivot axis 440'). In a still further embodiment shown in FIG. 8, a control device 830 includes a passive spring 838 that biases the first elongated member 432 and the second elongated member 434 toward or away (as shown) from each other, while another biasing actuator 836 (e.g., configured as a capstan pulling a cable) may selectively apply force between the first elongated member 432 and the second elongated member 434 in an opposite direction to the spring to force apart or draw together (as shown), respectively, the first elongated member 432 and the second elongated member 434. In such case, the biasing actuator 836 may be unidirectional (i.e., capable of applying force in only one direction).

Referring to FIG. 9, and as mentioned above, the control device 130 may include other actuators instead of or in addition the biasing actuator 436. A control device 930 is a variant of the control device 130, which may include the biasing actuator 436, and also include a brake actuator 944, inertial actuators 946, and/or mass actuators 948. The various mechanical actuators may be operated simultaneously to each other to overlay (e.g., superimpose) different tactile feedback simultaneously. For example, the biasing actuator 436 and/or the brake actuator 944 may provide a tactile output representing resistance from the physical device engaging the physical object, while the inertial actuators simultaneously vibrate to represent texture and/or friction, and/or while the mass actuators are simultaneously moved to represent movement of the physical device and/or the object. The control device 130 may also include a temperature device 949 (e.g., a resistance heater or Peltier device) to represent changing temperature (e.g., using fire tongs near a fireplace). It should be noted that while several different actuators are depicted and described with respect to FIG. 9, various ones of the actuators may be omitted, moved, or added, so as to provide different combinations of tactile output to the user.

The brake actuator 944 is configured to resist input from the user (e.g., the input torque $\tau_{input}$) to the control device 130. The brake actuator 944 may resist the input torque $\tau_{input}$ alone or in conjunction with the biasing actuator 436. The brake actuator 944 may have a higher capacity (e.g., torque capacity) to resist greater magnitudes of input torque from the user than the biasing actuator 436 (e.g., two times greater, five times greater, or more). The brake actuator 944, thereby, allows the control device 930 to provide tactile feedback simulating physical devices resembled by the virtual device 322, or interaction with physical objects resembled by the virtual subject 323, which require relatively high magnitude input forces to achieve movement. Such high magnitude movement resistance from the brake actuator 944 may, for example, resemble physical devices that are stuck open or closed (e.g., rusted scissors) or interaction with physical objects that require relatively high forces (e.g., cutting a thick branch, as opposed to cutting thin paper). While the brake actuator 944 is able to react to and resist the input torque $\tau_{input}$, the brake actuator 944 does not cause movement of the first elongated member 432 and the second elongated member 434 relative to each other.

The brake actuator 944 may, for example, frictionally engage the electric motor 436a (e.g., the shaft, rotor, or gear thereof) or the connecting member 436b, for example, by selectively applying a clamping force thereto, which may vary in magnitude to represent the required tactile feedback. In another example, the brake actuator 944 may be an active damper, such as those having a selectively variable viscosity fluid (e.g., magneto rheological), which may be coupled to the output shaft or rotor of the electric motor 436a.

As shown schematically, the brake actuator 944 may be located proximate the biasing actuator 436, for example, being co-located and/or integrated therewith. Alternatively, the brake actuator 944 may be located at the pivot axis 440' (e.g., applying a braking force between the first elongated member 432 and the second elongated member via the shaft 440). Still further, referring back to FIG. 6, a torque brake actuator 644 may be configured as a variable output or selectively activated linear damper (e.g., dashpot) that extends between the distal portions 432a, 434a of the first elongated member 432 and the second elongated member 434.

Referring again to FIG. 9, the inertial actuators 946 may be configured to provide tactile to feedback to the user, for example, at higher frequencies, lower amplitudes, and/or in different directions than the biasing actuator 436 and/or the brake actuator 944. The inertial actuators 946 may have no or negligible effect on biasing the first elongated member 432 relative to the second elongated member 434 (e.g., have no or negligible effect on the output torque $\tau_{output}$ of the control device 930).

The inertial actuators 946 vibrate the elongated member to which the inertial actuator 946 is coupled to provide the tactile output. The inertial actuators 946 provide a vibratory output (e.g., high frequency, low magnitude over a relatively long duration), which may resemble physical behavior (e.g., friction) of the physical device resembled by the virtual device 322 (e.g., the two blades of the scissors sliding against each other), physical behavior (e.g., texture) of the resembled physical device engaging the physical object resembled by the virtual subject 323 (e.g., the scissors cutting paper, fine fabric, or coarse fabric), and/or material of the physical device (e.g., metal devices having higher frequency than similar plastic devices). The frequency of the vibration output from the inertial actuators 946 may be varied to represent different physical devices (e.g., scissors made of different materials) and/or different physical objects (e.g., cutting fine or coarse fabric).

The inertial actuators 946 may also provide a pulsed output (e.g., higher magnitude over a relatively short duration), which may resemble impact of the physical device resembled by the virtual device 322 with another object resembled by the virtual subject 323 or the virtual environment object 324 (e.g., the scissors impacting such physical object).

The inertial actuators 946 may be haptic actuators having a mass that is rotated off-center to a center of mass thereof or that is moved linearly in a rapid or oscillatory manner. The inertial actuators 946 may apply force in plane with the relative motion of the first elongated member 432 and the second elongated member 434 (e.g., by having an axis of rotation parallel with the pivot axis 440'), or perpendicular to such plane (e.g., by having an axis of rotation perpendicular with the pivot axis 440'). The inertial actuators 946 may have a higher frequency capacity and/or quicker responsiveness than the biasing actuator 436.

The one or more inertial actuators 946 may be provided at various different locations on the control device 930, such as on one or both of the first elongated member 432 and the second elongated member 434, on the distal portions 432a, 434a or the proximal portions 432b, 434b, and/or near or distant from the pivot axis 440'). For example, as shown in FIG. 9, one inertial actuator 946 is coupled to the proximal portion 432b of the first elongated member 432, and another inertial actuator 946 is coupled to the proximal portion 434b of the second elongated member 432. Providing the inertial actuators 946 on the proximal portions 432b, 434b may be advantageous to more directly provide the tactile feedback to the user, rather than such feedback being transmitted from the distal portions 432a, 434a and through the pivot axis 440'. Furthermore, by providing two inertial actuators 946, different tactile feedback may be provided by each of the first elongated member 432 and the second elongated member 434, for example, representing one part of physical device engaging the physical object differently than the other part (e.g., one blade of the scissors engaging an object before the other blade).

While two inertial actuators 946 are shown, the control device 930 may include fewer (e.g., one) or more of the inertial actuators 946. Still further, multiple ones of the inertial actuators 946 may be configured to provide outputs at different frequencies and/or different magnitudes from each other simultaneously or at different times from each other.

Still referring to FIG. 9, the one or more mass actuators 948 are configured to provide the user with tactile feedback resembling physical behavior of the physical device, such as resembling a change of weight, for example, as the virtual subject 323 is moved by one or both elongated members of the virtual device 322. More particularly, the mass actuator 948 is configured to change a center of gravity of the control device 930. For example, moving the center of gravity away from the pivot axis 440' and, thereby, the user's hand, may resemble the physical object resembled by the virtual subject 323 being lifted by the physical device resembled by the virtual device 322.

Each mass actuator 948 may, for example, include an actuator component 948a (e.g., a linear actuator, such as a lead screw having an electric motor and a shaft) and a mass component 948b (e.g., a weight) that is moved by the actuator component 948a. For example, as shown, the distal portions 432a, 434a of the first and second elongated members 432, 434 each include one of the mass actuators 948, which move the mass component 948b toward and away from the pivot axis 440'. In a still further embodiment, the mass actuator 948 and the inertial actuator 946 may be integrated in which case the inertial actuator 946 forms the mass component 948b.

Referring back to FIG. 4, as referenced above, the one or more sensors are configured to receive inputs from the user. The sensors may be configured to receive inputs that reflect manners by which users may normally interface with the physical device resembled by the virtual device 322, such as by biasing pivotable members relative to each other. The sensors may also be configured to control the outputs of the actuators in manners that reflect the physical device corresponding to the virtual device 322. The one or more sensors may, for example, include position sensors, torque sensors, touch sensors, and/or orientation sensors.

The sensors may include a position sensor 438a configured to determine the relative position (e.g., relative angular position) of the first elongated member 432 to the second elongated member 434 (e.g., of the distal portions 432a, 434a thereof). The position sensor 438a, for example, allows the computing device 110 to determine the output torque $\tau_{output}$ to be provided by (e.g., requested from) the biasing actuator 436 and/or the brake actuator 944. Instead or additionally, the position sensor 438a provides feedback for the various actuators to achieve the requested outputs from the computing device 110. The outputs of the various actuators may correspond to the relative position of the first elongated member 432 to the second elongated member 434, such as by changing the output torque $\tau_{output}$ according to the position determined from the position sensor 438a. For example, the output torque $\tau_{output}$ from the biasing actuator 436 may change gradually as the first elongated member 432 and the second elongated member 434 are determined to move relative to each other. Such a gradual change in output may, for example, simulate physical behavior of the physical device resembled by the virtual device 322 (e.g., deflecting the spring in sprung garden shears), or interaction with the physical object resembled by the virtual subject 323 (e.g., compressing a spring or inflated ball). In another example, the output torque $\tau_{output}$ from the biasing actuator 436 and/or the brake actuator 944 may rapidly change according to the relative position. Such a rapid change in output may, for example, simulate physical behavior of the physical device engaging the physical object that are resembled in the virtual scene (e.g., garden shears suddenly cutting through a wood branch).

The position sensor 438a also allows the angular velocity and angular acceleration between the first elongated member 432 and the second elongated member 434 to be determined (e.g., determining changes of position with respect to time). The angular velocity may, for example, allow tactile outputs representing friction. For example, when cutting paper or cardboard with scissors, user input torque may be resisted with output torque commensurate with the angular velocity.

The appearance of the virtual device 322 may also be changed according to the relative positioned determined by the position sensor 438a, for example, depicting the virtual device 322 moving between the closed and open positions. As a result, the tactile feedback corresponds to the changes in the visual appearance of the virtual device 322.

The position sensor 438a may, for example, be a rotary encoder that measures an angular position of an output shaft of the electric motor 436a of the biasing actuator 436, a Hall effect sensor, or other suitable sensor. The position sensor 438a may instead be located at the pivot axis 440', or other types of sensors may be used to determine the position of the first elongated member 432 relative to the second elongated member 434 (e.g., optical sensors, flex sensors, or other suitable type of sensor). By providing the position sensor 438a in arrangements further from the pivot axis 440', the position sensor 438a may, however, provide greater accuracy (e.g., by measuring rotations of the electric motor 436a, as opposed to a partial rotation about the pivot axis 440').

The sensors may also include a torque sensor 438b (or force sensor), which is used to measure or determine the output torque $\tau_{output}$ of the control device 130 and/or input torque $\tau_{input}$ from the user. By measuring or monitoring the output torque $\tau_{output}$ of the control device 130 and/or the input torque $\tau_{input}$ from the user, the control device 130 may ensure that the proper output torque $\tau_{output}$ is output to provide appropriate tactile feedback to the user.

Referring to FIG. 9, instead of or in addition to the position sensor 438a and the torque sensor 438b, the control device 930 may include an orientation sensor 950, such as an inertial measurement unit (IMU), gyroscope, accelerometers, or other sensor(s) to determine movement, an orientation, and/or a position of the control device 930 in real space. From the movement, position, and/or orientation of the control device 930 as determined with the orientation sensor 950, the visual output of the display device 120 may be changed (e.g., by showing the virtual device 322 change position and/or orientation) and output of the control device 930 may be changed, for example, by operating the biasing actuator 436 and/or one or more of the mass actuators 948 (e.g., reflecting movement of the virtual device 322 and/or the virtual subject 323). One or more of the orientation sensors 950 may, for example, be coupled to one or both of the first elongated member 432 and the second elongated member 434 (e.g., the first elongated member 432, as shown, while orientation of the second elongated member 434 may be derived from the position sensor 438a along with the orientation sensor 950). The orientation sensor 950 allows movement of the control device 130 in space to be determined without being physically coupled to a ground location (e.g., a base).

The control device 930 may also include one or more touch sensors 952 configured to detect or otherwise sense the user with the control device 930. The touch sensor 952 may, for example, be a capacitive sensor, a pressure sensor, force sensor, or other type of suitable sensor. One of the touch sensors 952 may be connected to each of the proximal portions 432b, 434b of the first elongated member 432 and the second elongated member 434. The one or more touch sensors 952 may be used to determine appropriate outputs from the actuators of the control device 930. For example, the touch sensors 952 may measure force, which may be used to determine the input torque $\tau_{output}$ and/or to vary the output torque $\tau_{output}$ and/or whether any tactile output is provided (e.g., no tactile output is provided if the control device 930 is not detected to be held by the user).

The control device 930 may include still further types of sensors, such as compass. The interactive computing system 100 may also employ other sensors for detecting operation and/or movement of the control device 930, such as external observation cameras and related video recognition software for determining movement of the user and/or the control device 930 and/or manipulation of the control device 930.

Figure 10:
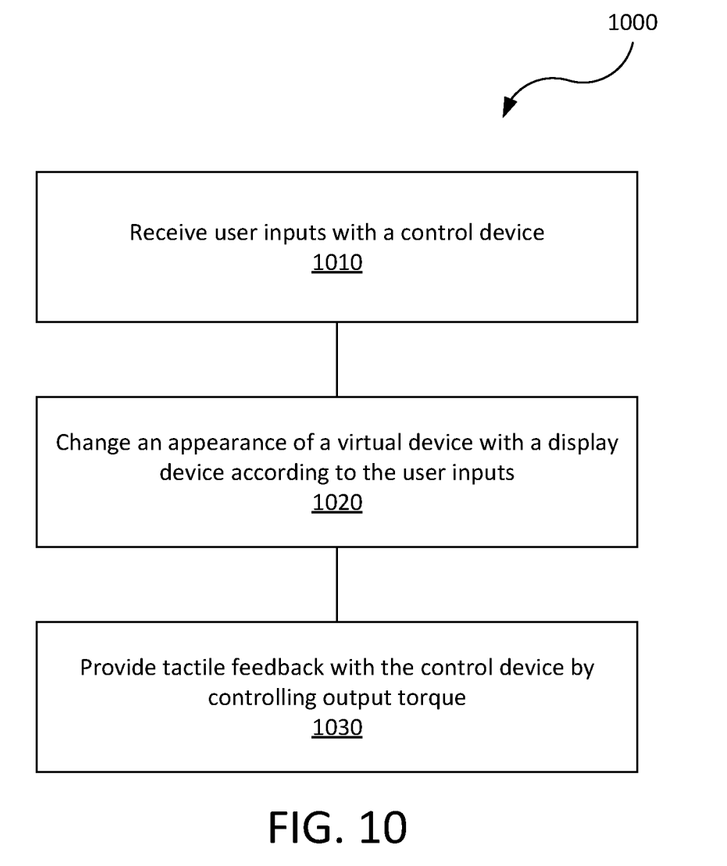
FIG. 10 is a flow diagram of a method for operating the interactive computing system of FIG. 1.

In accordance with the interactive computing system 100 described above, a method 1000 is provided for operating the interactive computing system. The method, which may be implemented with software stored and executed by the computing device 110, generally includes receiving 1010 user inputs with the control device (e.g., the control device 130, 430, 530, 630, 930, and variations and/or combinations thereof), changing 1020 an appearance of the virtual device according to the user inputs with a display device (e.g., the display device 120 as controlled by the computing device 110), and providing 1030 tactile feedback with the control device (e.g., as controlled by the computing device 110).

The receiving 1010 includes, for example, receiving the input torque $\tau_{input}$ (e.g., measured by the torque sensor 438b), the input force (e.g., measured with the touch sensor 952), movement of the elongated members 432, 434 relative to each other (e.g., measured with the position sensor 438a), and/or motion of the control device (e.g., with the orientation sensor 950).

The changing 1020 of the appearance of the virtual device is performed by the display device 120 as controlled by the computing device 110 according to the receiving 1010 of the user inputs. The changing 1020 of the appearance of the virtual device, for example, includes changing a shape or state of the virtual device (e.g., moving portions of the virtual device relative to each other, such as blades of scissors) and/or moving the virtual device relative to other virtual subjects in the virtual environment. Changing the state of the virtual device may be performed according to position of the elongated members 432, 434 of the control device relative to each other as measured by the position sensor 438a. Moving the virtual device with respect to the virtual environment may be performed according to movement of the control device relative to real space as measured by the orientation sensor 950. The changing 1020 of the appearance of the virtual device may also include changing the appearance of the virtual subject that is manipulated by the virtual device, for example, by changing the shape of and/or moving the virtual subject.

The providing 1030 of the tactile feedback is performed by the control device as controlled by the computing device 110 according to the receiving 1010 of the user inputs. The tactile feedback is further performed according to (e.g., to simulate) physical characteristics of the physical device and/or the physical object that are resembled by the virtual device and/or the virtual subject, respectively, as described above (e.g., according to the type of the physical device, the physical subject interacting therewith, and the physical characteristics thereof). The tactile feedback corresponds to the changing 1020 of the appearance of the virtual device and/or the virtual subject. The providing 1030 of tactile feedback, may include simultaneously controlling the output torque of the biasing actuator, along with controlling outputs of one or more of a brake actuator to resist motion of the control device, an inertial actuator to vibrate the control device, or a mass actuator to move a center of gravity of the control device.

Furthermore, receiving 1010, the changing 1020, and the providing 1030 may be performed for other virtual devices and/or other virtual subjects at another time. The other virtual devices and/or the other virtual subjects may resemble different physical devices and objects, respectively, which have different physical characteristics. As a result, the changing 1020 of the appearance of the other virtual device and the providing 1030 of the tactile feedback is performed differently to resemble the different physical behavior (e.g., the different physical characteristics) of the different physical device and the different physical subject.

Figure 11:
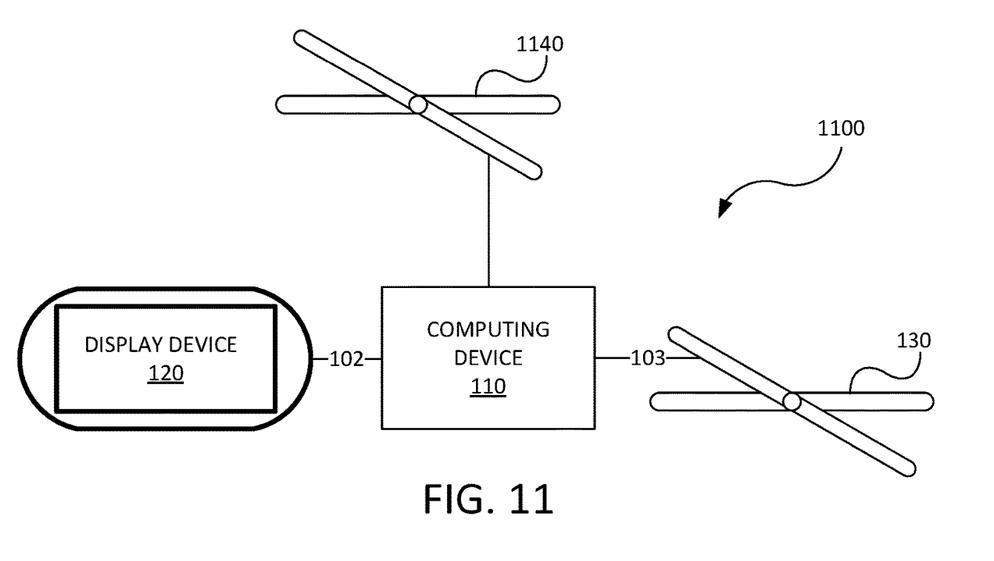
FIG. 11 is a schematic view of a robotic system.

The control device 130 and variations thereof have been described with respect to the interactive computing system 100 in which no mechanical output device is ultimately controlled with the control device 130. Referring to FIG. 11, the control device 130 may instead be used in a robotic system 1100 that includes a mechanical output device 1140 in addition to the computing device 110, the display device 120, and the control device 130. The mechanical output device 1140 is in communication with the computing device 110 and, in response to inputs received by the control device 130, produces mechanical outputs that may include interaction with a physical object. For example, the robotic system 1100 may be a surgical system.

In still further implementations, the display device 120 may be omitted from the interactive computing system 100 such that tactile feedback but not visual feedback is not provided, while audible feedback may also be provided.

What is claimed is:

1. A control device for an interactive computing system comprising:
   a first elongated member and a second elongated member that are pivotably coupled at a pivot axis;
   a biasing actuator coupled to the first elongated member and the second elongated member to provide an output torque between the first elongated member and the second elongated member about the pivot axis;
   wherein the control device is configured to receive user input for controlling a virtual device displayed by the interactive computing system to visually resemble a physical device, the biasing actuator is controllable to provide tactile feedback to simulate physical behavior of the physical device, and the control device is movable freely in space.

2. The control device according to claim 1, further comprising one or more additional actuators that include one or more of a brake actuator that resists input torque between the first elongated member and the second elongated member about the pivot axis, an inertial actuator that is coupled to and vibrates one of the first elongated member or the second elongated member, and a mass actuator that moves a center of gravity of the control device;
   wherein the one or more additional actuators are controllable to provide the tactile feedback.

3. The control device according to claim 2, comprising the brake actuator, wherein the biasing actuator is configured to move the first elongated member relative to the second elongated member, and the brake actuator is not configured to move the first elongated member relative to the second elongated member.

4. The control device according to claim 3, wherein the brake actuator has a higher capacity to resist the input torque than the biasing actuator.

5. The control device according to claim 2, comprising the inertial actuator coupled to the first elongated member, wherein the inertial actuator vibrates the first elongated member to provide the tactile feedback.

6. The control device according to claim 5, further comprising another inertial actuator coupled to the second elongated member, wherein the other inertial actuator vibrates the second elongated member to provide the tactile feedback.

7. The control device according to claim 2, comprising the mass actuator coupled to the first elongated member, wherein the mass actuator includes a mass that is selectively moveable relative to the first elongated member to change the center of gravity of the control device to provide the tactile feedback.

8. The control device according to claim 2, wherein the biasing actuator and the one or more additional actuators are simultaneously controllable to provide the tactile feedback.

9. The control device according to claim 2, comprising two or more of the brake actuator, the inertial actuator, or the mass actuator.

10. The control device according to claim 1, further comprising one or more sensors for receiving user input, the one or more sensors including one or more of a position sensor for determining a relative angular position between the first elongated member and the second elongated member about the pivot axis, a torque sensor for determining input torque applied to the first elongated member and the second elongated member about the pivot axis, or an orientation sensor determining an orientation of the control device.

11. The control device according to claim 10, comprising the position sensor, wherein the biasing actuator is controllable according to the relative angular position determined with the position sensor.

12. The control device according to claim 10, comprising the torque sensor, wherein the biasing actuator is controllable according to the input torque determined with the torque sensor.

13. The control device according to claim 10, comprising the orientation sensor, wherein the biasing actuator is controllable according to the orientation determined with the orientation sensor.

14. The control device according to claim 1, wherein the control device is freely movable in space by not being coupled to a mechanical device that measures movement of the control device.

15. An interactive computing system comprising:
   a user control device movable independent of a real environment, the user control device comprising:
      first and second members that are pivotably coupled to each other,
      a sensor for receiving a user input from a user applying input torque between the first and second members, and
      a biasing actuator that provides output torque between the first and second members;
   a display device that displays a virtual device simulating physical characteristics of a physical device; and
   a computing device in communication with the user control device and the display device, wherein the computing device receives the user input from the user control device, controls the display device to change an appearance of the virtual device according to the user input, and controls the biasing actuator to provide the output torque as tactile feedback of the physical characteristics corresponding to the change in appearance of the virtual device.

16. The interactive computing system according to claim 15, wherein the appearance of the virtual device is changed to resemble the physical characteristics of the physical device.

17. The interactive computing system according to claim 16, wherein the computing device controls the display device to display a virtual subject that depicts a physical object, controls the display device to change an appearance of the virtual device interacting with the virtual subject according to the user input, and controls the biasing actuator to provide the tactile feedback resembling physical behavior of the physical device interacting with the physical object.

18. The interactive computing system according to claim 15, wherein the user control device includes one or more additional actuators that are controlled according to the user input simultaneous with the biasing actuator to provide the tactile feedback, the one or more additional actuators including one or more of a brake actuator to resist input torque to the user control device, an inertial actuator to vibrate the user control device, or a mass actuator to change a center of gravity of the user control device.

19. The interactive computing system according to claim 15, wherein the physical device is a handheld tool having pivotable members.

20. The interactive computing system according to claim 15, wherein the computing device controls the display device to display different virtual devices that resemble different physical devices having different physical characteristics, and controls the biasing actuator to provide different tactile feedback that resembles the different physical characteristics of the different physical devices.

21. The interactive computing system according to claim 15, wherein the interactive computing system does not control a mechanical output device according to inputs received with the user control device.

22. The interactive computing system according to claim 15, wherein the display device displays the virtual device in a virtual environment.

23. A method of operating an interactive computing system comprising:
receiving user input from a control device having two members that are pivotable relative to each other and a biasing actuator that applies output torque between the two members, wherein the control device is freely movable;
changing with a display device an appearance of a virtual device according to the user input, the virtual device resembling a physical device having physical characteristics; and
providing tactile feedback with the control device by controlling the output torque of the control device with the biasing actuator to simulate the physical characteristics.

24. The method according to claim 23, wherein the user input includes input torque applied by a user between the two members.

25. The method according claim 23, wherein the control device includes one or more of a brake actuator, an inertial actuator, or a mass actuator, and the providing the tactile feedback includes controlling outputs of one or more of the brake actuator to resist movement between the two members, the inertial actuator to vibrate one or more of the two members, or the mass actuator to move a center of gravity of the control device.

26. An interactive computing system comprising:
a user control device movable independent of a real environment, the user control device comprising:
first and second members that are pivotably coupled to each other,
a sensor for receiving a user input from a user applying input torque between the first and second members, and
a biasing actuator that provides output torque between the first and second members;
a display device that displays a virtual device; and
a computing device in communication with the user control device and the display device, wherein the computing device receives the user input from the user control device, controls the display device to change an appearance of the virtual device according to the user input, and controls the biasing actuator to provide the output torque as tactile feedback corresponding to the change in appearance of the virtual device;
wherein the user control device includes one or more additional actuators that are controlled according to the user input simultaneous with the biasing actuator to provide the tactile feedback, the one or more additional actuators including one or more of a brake actuator to resist input torque to the user control device, an inertial actuator to vibrate the user control device, or a mass actuator to change a center of gravity of the user control device.

27. The interactive computing system according to claim 26, wherein the user control device comprises the brake actuator, wherein the biasing actuator is configured to move the first member relative to the second member, and the brake actuator is not configured to move the first member relative to the second member.

28. The interactive computing system according to claim 27, wherein the brake actuator has a higher capacity to resist the input torque than the biasing actuator.

29. The interactive computing system according to claim 26, wherein the user control device comprises the inertial actuator coupled to the first member, wherein the inertial actuator vibrates the first member to provide the tactile feedback.

30. The interactive computing system according to claim 29, wherein the user control device comprises another inertial actuator coupled to the second member, wherein the other inertial actuator vibrates the second member to provide the tactile feedback.

31. The interactive computing system according to claim 26, wherein the user control device comprises the mass actuator coupled to the first member, wherein the mass actuator includes a mass that is selectively moveable relative to the first member to change the center of gravity of the user control device to provide the tactile feedback.

32. The interactive computing system according to claim 26, wherein the biasing actuator and the one or more additional actuators are simultaneously controllable to provide the tactile feedback.

33. The interactive computing system according to claim 26, wherein the user control device comprises two or more of the brake actuator, the inertial actuator, or the mass actuator.

34. A method of operating an interactive computing system comprising:
receiving user input from a control device having two members that are pivotable relative to each other and a biasing actuator that applies output torque between the two members, wherein the control device is freely movable, and the two members include a first member and a second member;
changing with a display device an appearance of a virtual device according to the user input; and
providing tactile feedback with the control device by controlling the output torque of the control device with the biasing actuator;
wherein the control device includes one or more of a brake actuator, an inertial actuator, or a mass actuator, and the providing the tactile feedback includes controlling outputs of one or more of the brake actuator to resist movement between the two members, the inertial actuator to vibrate one or more of the two members, or the mass actuator to move a center of gravity of the control device.

35. The method according to claim 34, wherein the control device comprises the brake actuator, and wherein the biasing actuator is configured to move the first member relative to the second member, and the brake actuator is not configured to move the first member relative to the second member.

36. The method according to claim 35, wherein the brake actuator has a higher capacity to resist input torque than the biasing actuator, the input torque being the user input.

37. The method according to claim 34, wherein the control device comprises the inertial actuator coupled to the first member, wherein the inertial actuator vibrates the first member to provide the tactile feedback.

38. The method according to claim 37, wherein the control device comprises another inertial actuator coupled to the second member, wherein the other inertial actuator vibrates the second member to provide the tactile feedback.

39. The method according to claim 34, wherein the control device comprises the mass actuator coupled to the first member, wherein the mass actuator includes a mass that is selectively moveable relative to the first member to change the center of gravity of the control device to provide the tactile feedback.

40. The method according to claim 34, wherein the biasing actuator and the one or more of the brake actuator, the inertial actuator, or the mass actuator are simultaneously controllable to provide the tactile feedback.

41. The method according to claim 34, wherein the control device comprises two or more of the brake actuator, the inertial actuator, or the mass actuator.

\* \* \* \* \*